(12) United States Patent
Weiss et al.

(10) Patent No.: US 6,509,021 B1
(45) Date of Patent: Jan. 21, 2003

(54) USE OF MUTATED SUBTILISIN PROTEASE IN COSMETIC PRODUCTS

(75) Inventors: Albrecht Weiss, Langenfeld (DE); Karl-Heinz Maurer, Erkrath (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/011,889

(22) PCT Filed: Aug. 14, 1996

(86) PCT No.: PCT/EP96/03589

§ 371 (c)(1),
(2), (4) Date: Apr. 23, 1998

(87) PCT Pub. No.: WO97/07770

PCT Pub. Date: Mar. 6, 1997

(30) Foreign Application Priority Data

Aug. 23, 1995 (DE) .......................... 195 30 816

(51) Int. Cl.[7] .............................. A61K 7/00; C12N 9/54; C12N 15/57; C12N 15/75
(52) U.S. Cl. ....................... 424/401; 435/69.1; 435/221; 435/252.31; 435/320.1; 435/471; 536/23.2
(58) Field of Search ........................ 424/401; 435/221, 435/69.1, 252.31, 320.1; 536/23.2

(56) References Cited

U.S. PATENT DOCUMENTS

| | | | |
|---|---|---|---|
| 4,760,025 A | | 7/1988 | Estell et al. ............... 435/222 |
| 5,230,891 A | * | 7/1993 | Nakayama et al. .......... 424/401 |
| 5,340,735 A | * | 8/1994 | Christianson et al. ....... 435/221 |
| 5,700,676 A | * | 12/1997 | Bott et al. ................. 435/221 |
| 5,703,041 A | * | 12/1997 | Afriat et al. .................. 514/2 |
| 5,801,039 A | * | 9/1998 | Maurer et al. .............. 435/221 |
| 5,855,625 A | * | 1/1999 | Maurer et al. ................. 8/137 |
| 5,935,559 A | * | 8/1999 | Afriat et al. ............. 424/70.12 |

FOREIGN PATENT DOCUMENTS

| | | | |
|---|---|---|---|
| EP | 0 130 756 | | 1/1985 |
| EP | 0 247 647 | | 12/1987 |
| EP | 0 260 105 | | 3/1988 |
| EP | 0 328 229 | | 8/1989 |
| EP | 0571049 | * | 11/1993 |
| WO | WO91/00345 | | 1/1991 |
| WO | WO91/02792 | | 3/1991 |
| WO | WO92/11357 | | 7/1992 |
| WO | WO92/21760 | | 12/1992 |
| WO | WO 92/21760 | * | 12/1992 |
| WO | WO 94/02618 | * | 2/1994 |
| WO | WO94/02618 | | 2/1994 |
| WO | WO94/21760 | | 9/1994 |
| WO | WO95/10591 | | 4/1995 |
| WO | WO 95/10591 | * | 4/1995 |
| WO | WO 95/10615 | * | 4/1995 |
| WO | WO95/23221 | | 8/1995 |
| WO | WO 95/30011 | * | 11/1995 |

OTHER PUBLICATIONS

Siezen, R. J., et al., 1991, "Homology modelling and protein engineering strategy of subtilases, the family of subtilisin–like serine proteases", Protein Engineering, vol. 4, pp. 710–737.*
Eur. J. Biochem. 178:155–171 (1988).
J. Biol. Chem. 263: 7895–7906 (1988).
J. Mol. Biol. 228: 580–95 (1992).
J. Mol. Biol. 217: 353–71 (1991).
Ann. Rev. Biochem. 46: 331–58 (1977).
Protein Eng. 2: 271–76 (1988).
J. Mol. Biol. 214: 261–79 (1988).
J. Biol. Chem. 260: 6518–21 (1985).
Proc. Natl. Sci. USA 86: 6562–6566 (1989).
Biochemistry 27: 8311–17 (1988).
Nature 328: 496–500 (1987).
Chimicaoggi 31–35 (Jul./Aug. 1991).
Trends Biochem. Sci. 13: 291–297 (1988).
J. Mol. Biol. 193: 803–13 (1987).
"Kosmetische Faerbemittel, Colours for Cosmetics", der Farbstoffkommission der deutschen Forschungsgemein-schaft, Verlag Chemie, 55–61 (1984).
Tenside 7: 125 (1970).
Arch: Dermatol. 91: 171–177 (1965).

* cited by examiner

Primary Examiner—Ponnathapu Achutamurthy
Assistant Examiner—William W. Moore
(74) Attorney, Agent, or Firm—Stephen D. Harper; Glenn E. J. Murphy

(57) ABSTRACT

A mutated subtilisin-type protease that bears at least one mutation in its amino-acid sequence that causes the positive charge to be reduced or the negative charge to be increased in the substrate binding region of the molecule is used in cosmetic products. Such proteases show a surprisingly low skin and mucous membrane irritating potential.

17 Claims, No Drawings

USE OF MUTATED SUBTILISIN PROTEASE IN COSMETIC PRODUCTS

CROSS REFERENCE TO RELATED APPLICATIONS

This application is a national stage application under 35 U.S.C. § 371 of international application PCT/EP96/03589 filed on Aug. 14, 1996, the international application not being published in English. This application also claims priority under 35 U.S.C. § 119 to DE 195 30 816.6, filed on Aug. 23, 1995.

BACKGROUND OF THE INVENTION

1. Field of the Invention

This invention relates to the use of mutated proteolytic enzymes with a low skin irritation potential, namely mutated subtilisin proteases, in cosmetic products, more particularly body-cleansing and body-care formulations and oral hygiene formulations.

Enzymes, such as proteases, lipases, amylases and cellulases, have long been used in detergents and cleaners—essentially to support their washing and cleaning performance. Among these enzymes, proteases occupy a position of paramount importance.

2. Discussion of the Related Art

Proteases are enzymes which catalyze the hydrolysis of peptide bonds in protein and peptide substrates and of ester bonds in certain terminal esters. Subtilisins are a family of bacterial extracellular proteases with molecular weights of about 20,000 to 45,000 dalton which can be obtained from soil bacteria, for example Bacillus amyloliquefaciens. Subtilisins belong to the group of serine proteases which initiate the nucleophilic attack on the peptide (ester) bond through a serine residue at the active site. They are physically and chemically well characterized enzymes. The three-dimensional structure of certain subtilisins was elucidated in detail by X-ray diffractograms (C. Betzel, G. P. Pal and W Saenger, (1988) Eur. J. Biochem. 178, 155–171; R. Bott, M. Ultsch, A. Kossiakoff, T. Graycar, B. Kartz and S. Power, (1988) J. Biol Chem. 263, 7895–7906; D. W. Goddette, C. Paech, S. S. Yang, J. R. Mielenz, C. Bystroff, M. Wilke and R. J. Fletterick, (1992) J. Mol. Biol. 228, 580–595; D. W. Heinz, J. P. Priestle, J. Rahuel, K. S. Wilson and M. G. Grütter (1991) J. Mol. Biol. 217, 353–371; J. Kraut (1977) Ann. Rev. Biochem. 46, 331–358; D. J. Neidhart and G. A. Petsko (1988) Protein Eng. 2, 271–276; A. V. Teplyakov, I. P. Kuranova, E. H. Harutyunyan, B. K Vainshtein, C. Frömmel, W.-E. Höhne und K. S. Wilson (1990) J. Mol. Biol. 214, 261–279).

Subtilisins are widely used in commercial products, for example in laundry and dishwashing detergents and in contact lens cleaners, and—above all for research purposes—in synthetic organic chemistry. One member of the subtilisin family, namely a highly alkaline protease which can be used in surfactant-containing formulations, is described in International patent application WO 91/02792. This alkaline protease from *Bacillus lentus* (*Bacillus lentus* alkaline protease; BLAP) can be obtained in commercially useful quantities from the strain *Bacillus licheniformis* ATCC 53926 which carries an expression plasmid that expresses the BLAP gene under the control of the promoter of the alkaline protease of *Bacillus licheniformis* ATCC 53926. The crystal structure of BLAP has been determined (D. W. Goddette et al. (1992) J. Mol. Biol. 228, 580–595; WO 92/21760) and the coordinates were deposited at the Brookhaven Protein Data Bank. If an optimal sequence homology of BLAP (269 amino acids) is aligned with that of subtilisin BPN' (275 amino acids), the following pattern is obtained: the BLAP positions 1 to 35, 36 to 54, 55 to 160 and 161 to 269 correspond to positions 1 to 35, 37 to 55, 57 to 162 and 167 to 275, respectively, in subtilisin BPN'. Unless otherwise indicated, the numbering of the amino acids used in the present specification corresponds to that of BLAP.

The following nomenclature is used to describe the protease variants employed in the present invention: [original amino acid; position of the N terminus of the ripe enzyme; substituted amino acid]. For example, the replacement of valine by isoleucine in position 4 in BLAP is designated V4I. The list of the standard abbreviations for the typical amino acids is given in Table 1.

TABLE 1

Abbreviations of the amino acids

| | | |
|---|---|---|
| A = | Ala = | Alanine |
| C = | Cys = | Cysteine |
| D = | Asp = | Aspartic acid |
| E = | Glu = | Glutamic acid |
| F = | Phe = | Phenyl alanine |
| G = | Gly = | Glycine |
| H = | His = | Histidine |
| I = | Ile = | Isoleucine |
| K = | Lys = | Lysine |
| L = | Leu = | Leucine |
| M = | Met = | Methionine |
| N = | Asn = | Asparagine |
| P = | Pro = | Proline |
| Q = | Gln = | Glutamine |
| R = | Arg = | Arginine |
| S = | Ser = | Serine |
| T = | Thr = | Threonine |
| V = | Val = | Valine |
| W = | Trp = | Tryptophan |
| Y = | Tyr = | Tyrosine |

Where several mutations occur within the same protein molecule, this is characterized through the sum of the individual mutations, such as for example S3T+V4I+A188P+V193M+V199I.

Protection against thermal and chemical inactivation and improvement of washing and cleaning performance and dermatological compatibility are primary functions if new proteases are to be developed for industrial and institutional applications. Several enzymes, including proteases of the subtilisin type, have been developed by random mutagenesis or site-specific mutagenesis. They provide some indicators as to how improved thermal and chemical stability can be rationally achieved (D. A. Estell, T. P. Graycar and J. A. Wells (1985) J. Biol. Chem. 260, 6518–6521; M. Matsumura, W. J. Becktel, M. Levitt and B. W. Matthews (1989) Proc. Natl. Sci. US 86, 6562–6566; M. W. Pantoliano, M. Whitlow, J. F. Wood, M. L. Rollence, B. C. Finzel, G. L. Gilliland, T. L. Poulos and P. N. Bryan (1988) Biochemistry 27, 8311–8317; A. J. Russell and A. R. Fersht (1987) Nature 328, 496–500; R. J. Siezen, W. M. De Vos, J. A. M. Leunissen and B. W. Dijkstra (1991) Protein Eng. 4, 719–737; J. H. van Ee (1991) Chimicaoggi (7/8), 31–35; J. A. Wells and D. A. Estell (1988) Trends Biochem. Sci. 13, 291–297). By contrast, the modification of enzymatic activity, particularly improving or optimizing the activity rate for certain substrates, is a far more complex problem. EP 0 260 105 discloses the production of subtilisin-BPN'-mutants with modified ratios of transesterification rate to hydrolysis rate and nucleophilic specificities by modifying specific amino acid residues within 15 Å of the catalytic triad. A. J. Russell and A. R. Fersht (1987), J. Mol. Biol 193, 803–813, describe the isolation of a subtilisin-BPN'-mutant (DO99S) which has a modification to the surface charge at a distance of 14 to 15 Å from the active center. This substitution influences the pH dependence of the catalytic reaction of the subtilisin. None of these publications teaches whether the modifications to the amino acids also produce a change in the dermatological compatibility of the enzymes. EP 0 130 756, EP 0 247 647 and U.S. Pat. No. 4,760,025 disclose a saturation mutation process in which at least one mutation is inserted into the subtilisin BPN' at the amino acid residues (BPN' numbering) Asp32, Asn 155, Tyr104, Met222, Gly166, His64, Ser221, Gly169, Glu156, Ser33, Phe189, Tyr217 and/or Ala152. Mutated proteases which show improved oxidative stability, modified substrate specificity and/or modified pH activity are obtained using this procedure. The documents in question also teach that mutations in the vicinity of the active center of the protease have the most influence on activity. However, none of the documents in question discloses a process with which it is possible to predict whether and which changes in the amino acid sequence improve the dermatological compatibility of proteases.

Most of the information on the catalytic activity of subtilisins has been gathered in investigations into the hydrolysis of small well-defined peptide substrates. Hitherto, little has been known about interactions with large protein substrates. This applies in particular to information on the washing performance of proteases when their substrate is bound to a textile surface and the catalysis has to take place in the presence of substances which interact with the enzyme, such as bleaching agents, surfactants and builders. In addition, nothing is known of the interaction of proteases with the substances normally present in skin-care and hair-care products and in oral hygiene products.

EP 0 328 229 discloses the isolation and characterization of PB92 subtilisin mutants with improved properties when used in detergents on the basis of the results of washing tests. This document teaches that biochemical properties are not reliable parameters for predicting enzyme performance in washing. Processes mentioned therein for selecting mutations comprise the substitution of amino acids by other amino acids in the same category (polar, non-polar, aromatic, charged, aliphatic and neutral), the substitution of polar amino acids, such as asparagine and glutamine, by charged amino acids and the increase in the anionic character of the protease at the mutation sites which do not belong to the active centers. There is no mention of a process for identifying which specific amino acids should be modified.

There are several patent applications which describe modifications of subtilisin enzymes for improving their mode of action in detergents, for example International patent applications WO 91/00345 and WO 92/11357.

European patent application EP 0 571 049 discloses certain mutated proteolytic enzymes. These enzymes are said to be at least 70% homologous with the amino acid sequence of the PB92 serine protease and to differ from the PB92 serine protease in at least one amino acid at positions 99, 102, 116, 126, 127, 128, 130, 160, 203, 211 and/or 212. The mutated protease is produced by growing a host strain transformed with an expression vector which contains a DNA sequence and which codes for the desired mutated protease.

Hitherto unpublished International patent application WO 95/23221 describes mutated proteases which, when added to detergents and cleaners, improve their effectiveness.

The problem addressed by the present invention was to provide mutated proteases which would show improved dermatological compatibility by comparison with the original protease and which would be suitable for use in cosmetic products, particularly body-cleaning and body-care formulations and oral hygiene formulations.

DESCRIPTION OF THE INVENTION

It has surprisingly been found that the mutated proteases mentioned in WO 95/23221 in particular satisfy this requirement.

The present invention relates to the use of mutated subtilisin protease in cosmetic products which is characterized in that the mutated subtilisin protease contains at least one mutation in its amino acid sequence which leads to a reduced positive charge or to an increased negative charge in the vicinity of that region of the molecule which is bound to the substrate ("substrate-binding region").

Cosmetic products in which the mutated protease may be used in accordance with the invention include, in particular, body-cleaning and body-care formulations and oral hygiene formulations, for example soaps in solid and liquid form, peeling cremes, skin cremes, soft cremes, nourishing cremes, sun protection cremes, night cremes, skin oils, skin-care lotions and body aerosols, deodorants, shaving cremes and shaving foams, hair shampoos, hair rinses and foam baths, mouthwashes and toothpastes.

Surprisingly, the mutated proteases to be used in accordance with the invention show a low potential for irritating the skin and mucous membrane and, accordingly, are eminently suitable for use in the products mentioned above.

The present invention also relates to the use of the proteases mentioned above for the production of skin-care, hair-care and body-care formulations. To produce these formulations, the individual components are mixed in known manner. The formulations in question, particularly where they contain lipophilic substances, may be present both as "water-in-oil" and as "oil-in-water" emulsions and may contain other typical auxiliaries and additives.

Besides the proteases used in accordance with the invention as essential ingredients, the formulations may contain in particular surfactants, such as anionic, nonionic, cationic, amphoteric and/or zwitterionic surfactants.

Suitable auxiliaries and additives are, for example, emulsifiers, oil components, fats and waxes, thickeners, superfatting agents, biogenic agents, film formers, fragrances, dyes, pearlescers, preservatives and pH regulators.

Typical oil components are such substances are paraffin oil, vegetable oils, fatty acid esters, silicone oils, dialkyl ethers, fatty alcohols and Guerbet alcohols, squalane and 2-octyl dodecanol, while suitable fats and waxes are, for example, spermaceti, beeswax, montan wax, paraffin and cetostearyl alcohol.

Suitable emulsifiers are, for example, sorbitan esters, monoglycerides, polysorbates, polyethylene glycol mono/ difatty acid esters, highly ethoxylated fatty acid esters and high molecular weight silicone compounds, for example dimethyl polysiloxanes with an average molecular weight of 10,000 to 50,000.

The superfatting agents used include such substances as polyethoxylated lanolin derivatives, dicytin derivatives and fatty acid alkanolamides, the fatty acid alkanolamides also serving as foam stabilizers.

Suitable thickeners are, for example, polysaccharides, more particularly xanthan gum, guar, agar agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone and electrolytes, such as sodium chloride and ammonium chloride.

Biogenic agents in the context of the invention are, for example, plant extracts, protein hydrolyzates and vitamin complexes.

Typical film formers are, for example, polyvinyl pyrrolidone, vinyl pyrrolidone/vinyl acetate copolymers, polymers of the acrylic acid series, quaternary cellulose derivatives and similar compounds.

Suitable preservatives are, for example, formaldehyde solutions, p-hydroxybenzoic acid esters or sorbic acid.

Pearlescers may be selected, for example, from glycol distearic acid esters, such as ethylene glycol distearate, and from fatty acid monoglycol esters.

Suitable dyes are any of the substances suitable and licensed for cosmetic purposes as listed, for example, in the publication entitled "Kosmetische Färbemittel" of the Farbstoffkommission der deutschen Forschungsgemeinschaft, published by Verlag Chemie, Weinheim, 1984. These dyes are normally used in concentrations of 0.001 to 0.1% by weight, based on the mixture as a whole.

Cremes in particular may contain—optionally in addition to the additives already mentioned—antioxidants such as, for example, butyl hydroxytoluene and tocopherol, moisturizers such as, for example, glycerol, sorbitol, 2-pyrrolidine-5-carboxylate, dibutyl phthalate, gelatin, polyglycols with an average molecular weight of 200 to 600, pH buffers such as, for example, the lactic acid/triethanolamine or lactic acid/NaOH system, mild surfactants such as, for example, alkyl oligoglucosides, fatty alcohol ether sulfates, fatty acid isethionates, taurides and sarcosinates, ether carboxylic acids, sulfosuccinates, protein hydrolyzates and fatty acid condensates, sulfotriglycerides, short-chain glucamides, phospholipids, plant extracts, for example extracts of Aloe vera, sun protection agents such as, for example, ultrafine titanium dioxide or organic substances, such as p-aminobenzoic acid and esters thereof, ethylhexyl-p-methoxycinnamic acid ester, 2-ethoxyethyl-p-methoxycinnamic acid ester, butyl methoxydibenzoyl methane and mixtures thereof and so-called active-substance accelerators, more particularly essential oils such as, for example, eucalyptus oil, menthol and the like.

In order to be able to use proteases in formulations of the type mentioned above, they should produce only very slight, if any, irritation of the skin and mucous membranes.

The original protease type from which the mutated proteases to be used in accordance with the invention are derived is preferably an above-described alkaline *Bacillus lentus* protease (BLAP) which is obtained from the strain DSM 5483 and which has 269 amino acid units, a molecular weight of 26,823 dalton and a calculated isoelectric point of 9.7, based on pK standard values. The BLAP gene can be obtained in known manner by isolation of the chromosomal DNA from the *B. lentus* strain DSM 5483, preparation of DNA samples with a homology against the DNA sequences of the regions coding for the *B. lentus* protease, production of genome libraries from the isolated chromosomal DNA and selection of the libraries for the interesting genes by hybridization of the samples. Mutants of the BLAP mentioned with improved stability to heat and surfactants are described in International patent application WO 92/21760.

It has now been found that a reduced skin and mucous membrane irritation potential can be obtained by carrying out amino acid modifications within the substrate-binding region of the enzyme which lead to an increase in the negative charge. According to the present invention, this can be done, for example, by increasing negatively charged amino acid residues or reducing positively charged amino acids residues in the substrate-binding region within a radius of 7 Å, the substrate-binding region being locatable with the aid of a bound substrate molecule such as, for example, MPF. In particular, amino acid modifications at positions 99, 154 and 211 in the BLAP variants M130 and M131 of *Bacillus lentus* known from WO 94/21760 lead to a reduced skin and mucous membrane irritation potential. The mutant M130 contains four amino acid modifications by comparison with native BLAP: S3T, A188P, V193M and V199I. The mutant M131 contains five amino acid modifications by comparison with native BLAP: S3T, V4I, A188P, V193M and V199I. The amino acid sequence for the protease M130 or M131 is reproduced in SEQ ID No. 2 or SEQ ID No. 1 of International patent application WO 92/21760. M130 and M131 may serve as a basis for further amino acid modifications for obtaining proteases with a reduced irritation potential. Preferred protease mutants for the use according to the invention are those obtained by replacement of at least one amino acid of the proteases M130 or M131 in which the amino acid is selected from the group consisting of arginine at position 99, serine at position 154 and leucine at position 211. These mutants and their production are disclosed in International patent application WO 95/23221 and are designated there as F11 (S3T+R99S+A188P+V193M+V199I), F43 (S3T+V4I+R99G+A188P+V193M+V199I), F44 (S3T+V4I+R99A+A188P+V193M+V199I), F45 (S3T+V4I+R99S+A188P+V193M+V199I), F46 (S3T+V4I+S154E+A188P+V193M+V199I), F47 (S3T+V4I+S154D+A188P+V193M+V199I), F49 (S3T+V4I+A188P+V193M+V199I+L211D), F54 (S3T+V4I+R99G+A188P+V193+V199I+L211D) and F55 (S3T+V4I+S154D+A188P+V193M+V199I+L211D ). The proteolytic activity may be measured as follows using the method described in Tenside 7 (1970) 125, i.e. by discontinuous determination using casein as substrate: the concentrations of the substrate solution are 12 mg per ml casein (prepared in accordance with Hammarsten; supplier: Merck, Darmstadt, No. 2242) and 30 mM tris in synthetic tap water (aqueous solution of 0.029% (weight/v) $CaCl_2 \cdot 2H_2O$, 0.014% (weight/v) $MgCl_2 \cdot 6H_2O$ and 0.021% (weight/v) $NaHCO_3$) with a hardness of 15°dH (German hardness). The substrate solution is heated to 70° C. and the pH is adjusted to 8.5 with 0.1 N NaOH at 50° C. The protease solution is prepared with 2% (weight/v) of anhydrous pentasodium tripolyphosphate in synthetic tap water, the pH being adjusted to 8.5 with hydrochloric acid. 200 μl of the enzyme solution are added to 600 μl of the casein substrate solution. The mixture is incubated for 15 minutes at 50° C. The reaction is terminated by addition of 600 μl of 0.44 M trichloroacetic acid (TCA) and 0.22 M sodium acetate in 3% (VN) acetic acid. After cooling on ice for 15 minutes, the TCA-insoluble protein is removed by centrifugation, an aliquot of 900 μl is mixed with 300 μl of 2 N NaOH and the extinction of the resulting mixture which contains TCA-soluble peptides is measured at 290 nm. Control values are obtained by adding 600 μl of the TCA solution to 600 μl of casein solution followed by 200 μl of enzyme solution. By definition a protease solution which produces a change in extinction of 0.550 OD at 290 nm under the conditions of this test has an activity of 10 PU per ml.

EXAMPLES

Example 1

Determination of the Irritation Potential

The irritation potential of proteases to be used in accordance with the invention was investigated using F49 and— for comparison—BLAP as examples. It was determined on guinea pigs in the course of the Buehler Test for dose determination (E. V. Buehler, Arch. Dermatol. 1965, 91, 171–177). To this end, a 10% solution of the protease was topically applied to the shaved skin and fixed for 6 hours by means of a bandage (Scotchpak® Non-Woven Patch, a product of Minnesota Mining and Manufacturing Company). The areas of skin of interest were evaluated 24, 48 and 72 hours after removal of the bandages.

These tests were carried out on four guinea pigs (strain: "Pirbright white"), the solutions being applied in at least two places per animal. The results are set out in Tables 2 and 3 below and represent mean values of erythema and odema formation. The results show that the mutated protease to be used in accordance with the invention has a far lower irritation potential than the unmodified protease BLAP.

In the Tables, the figures 0, 1 and 2 stand for the number of areas of skin on an animal where skin irritation was observed, s stands for slight crust formation at the margins of the treated skin areas and a stands for swelling.

What is claimed is:

1. A cosmetic composition comprising:
   (a) at least one mutant *Bacillus lentus* alkaline protease, wherein the mutant protease comprises a *Bacillus lentus* alkaline protease having one or more amino acid substitutions in its amino acid sequence, wherein at least one of the substitutions is at a position selected from 99, 154, or 211 or combinations thereof relative to the unmodified *Bacillus lentus* alkaline protease, leads to a reduced positive charge or an increased negative charge, and results in the mutant protease having reduced tissue surface irritation relative to the modified or unmodified *Bacillus lentus* alkaline protease not having these substitutions; and
   (b) one or more cosmetic materials compatible with said mutant protease.

2. The cosmetic composition of claim 1, wherein the mutant protease is a protease M130, or a protease M131, or both a protease M130 and a protease M131, and wherein said mutant protease comprises one or more amino acid

TABLE 2

Epidermal application of F49

| Animal No. | Body weight on day - 5 (g) | Concentration (w/w) | Activity (PU/ml) | After 24 h Erythema | Odema | After 48 h Erythema | Odema | After 72 h Erythema | Odema | Body weight on day - 7 (g) |
|---|---|---|---|---|---|---|---|---|---|---|
| 5 | 347 | 10.52 | 20000 | 1 | 0 | 2a | 2 | 2a | 2 | 359 |
|   |     | 5.26  | 10000 | 1 | 0 | 1  | 0 | 1a | 0 |     |
| 6 | 391 | 10.52 | 20000 | 1 | 0 | 1  | 2 | 1a | 2 | 403 |
|   |     | 5.26  | 10000 | 1 | 0 | 1  | 0 | 1a | 0 |     |
| 7 | 400 | 2.63  | 5000  | 1 | 0 | 1  | 0 | 1  | 0 | 416 |
|   |     | 1.31  | 2500  | 0 | 0 | 0  | 0 | 0  | 0 |     |
|   |     | 0.52  | 1000  | 0 | 0 | 0  | 0 | 0  | 0 |     |
|   |     | 0.26  | 500   | 0 | 0 | 0  | 0 | 0  | 0 |     |
| 8 | 379 | 2.63  | 5000  | 1 | 0 | 1  | 0 | 1a | 0 | 393 |
|   |     | 1.31  | 2500  | 0 | 0 | 0  | 0 | 0  | 0 |     |
|   |     | 0.52  | 1000  | 0 | 0 | 0  | 0 | 0  | 0 |     |
|   |     | 0.26  | 500   | 0 | 0 | 0  | 0 | 0  | 0 |     |

Observed systemic symptoms: none

TABLE 3

Epidermal application of BLAP (comparison)

| Animal No. | Body weight on day - 5 (g) | Concentration (w/w) | Activity (PU/ml) | After 24 h Erythema | Odema | After 48 h Erythema | Odema | After 72 h Erythema | Odema | Body weight on day - 7 (g) |
|---|---|---|---|---|---|---|---|---|---|---|
| 1 | 351 | 8.60 | 20000 | 1a | 0 | 2as | 2 | 2as | 2 | 355 |
|   |     | 4.30 | 10000 | 1  | 0 | 1   | 0 | 1s  | 0 |     |
| 2 | 325 | 8.60 | 20000 | 1a | 0 | 2as | 2 | 2as | 2 | 345 |
|   |     | 4.30 | 10000 | 1  | 0 | 1   | 1 | 1s  | 0 |     |
| 3 | 372 | 2.15 | 5000  | 1  | 0 | 2   | 1 | 2s  | 2 | 368 |
|   |     | 1.07 | 2500  | 1  | 0 | 0   | 0 | 0   | 0 |     |
|   |     | 0.42 | 1000  | 0  | 0 | 0   | 0 | 0   | 0 |     |
|   |     | 0.21 | 500   | 0  | 0 | 0   | 0 | 0   | 0 |     |
| 4 | 362 | 2.15 | 5000  | 1  | 0 | 2   | 2 | 2s  | 1 | 377 |
|   |     | 1.07 | 2500  | 0  | 0 | 1   | 0 | 1s  | 0 |     |
|   |     | 0.42 | 1000  | 0  | 0 | 1   | 0 | 1   | 0 |     |
|   |     | 0.21 | 500   | 0  | 0 | 0   | 0 | 0   | 0 |     |

Observed systemic symptoms: none substitutions at a position selected from 99, 154, or 211, or combinations thereof.

3. A cosmetic composition comprising
   (a) at least one mutant *Bacillus lentus* alkaline protease, wherein the mutant protease is a protease M130 or a protease M131 modified by one or more amino acid substitutions, wherein at least one of the amino acid substitutions is at a position selected from 99, 154, or 211 or combinations thereof relative to the unmodified *Bacillus lentus* alkaline protease from which the M130 protease or M131 protease is obtained, wherein the substitution at a position selected from 99, 154, or 211 or combinations thereof leads to a reduced positive charge or an increased negative charge, and results in the mutant protease having reduced tissue surface irritation relative to the M130 protease or M131 protease not having this substitution; and
   (b) one or more cosmetic materials compatible with said mutant protease.

4. The cosmetic composition of claim 3, wherein the mutant protease has an amino acid substitution at position 99 relative to the unmodified *Bacillus lentus* alkaline protease and the substituent amino acid is selected from glycine, alagite, or serine.

5. The cosmetic composition of claim 3, wherein the mutant protease has an amino acid substitution at position 154 relative to the unmodified *Bacillus lentus* alkaline protease and the substituent amino acid is glutanic acid or aspartic acid.

6. The cosmetic composition of claim 3, wherein the mutant protease as an amino acid substitution at position 211 relative to the unmodified *Bacillus lentus* alkaline protease and the substituent amino acid is glutamic acid or aspartic acid.

7. The cosmetic composition of claim 3, wherein the mutant protease has one or more mutations selected from the group consisting of R99G, R99S, R99A, L211D), L211E, S154D, and S154E.

8. A method of avoiding or reducing tissue surface irritation due to contact with a protease containing cosmetic composition, comprising contacting a tissue surface with a cosmetic composition comprising at least one mutant *Bacillus lentus* alkaline protease, wherein the mutant protease comprises a *Bacillus lentus* alkaline protease having one or more no acid substitutions in its amino acid sequence, wherein at least one of the substitutions (i) occurs at a position lying within a 7 Å radius of the substrate binding region of the unmodified *Bacillus lentus* alkaline protease, (ii) leads to a reduced positive charge or an increased negative charge and (iii) results in the mutant protease having reduced tissue surface irritation relative to the modified or unmodified *Bacillus lentus* alkaline protease not having these substitutions within the 7 Å radius.

9. The method of claim 8, wherein at least one of the substitutions within the 7 Å radius of the substrate binding region that leads to the reduced positive charge or increased negative charge is at a position selected from 99, 154, or 211 or combinations thereof, relative to the unmodified *Bacillus lentus* alkaline protease.

10. The method of claim 9, wherein the mutant protease has one or more substitutions selected from the group consisting of R99G, R99S, R99A, L211D, L211E, S154D, and S154E.

11. The method of claim 8 wherein the mutant protease is a protease M130, or a protease M131, or both a protease M130 and a protease M131, and wherein said mutant protease is modified by one or more amino acid substitutions in its amino acid sequence at a position that lies within a 7 Å radius of the substrate binding region of the unmodified *Bacillus lentus* alkaline protease, wherein said one or more amino acid substitutions leads to a reduced positive charge or an increased negative charge.

12. The method of claim 11, wherein the mutant protease has one or more amino acid substitutions at a position selected from 99, 154, or 211 or combinations thereof relative to the unmodified *Bacillus lentus* alkaline protease.

13. A method of preparing a cosmetic composition, comprising mixing at least one mutant *Bacillus lentus* alkaline protease with at least one cosmetic material compatible with the mutant protease, wherein the mutant protease comprises a *Bacillus lentus* alkaline protease having one or more amino acid substitutions in its amino acid sequence, wherein at least one of the substitutions (i) occurs at a position lying within a 7 Å radius of the substrate binding region of the unmodified *Bacillus lentus* alkaline protease, (ii) leads to a reduced positive charge or an increased negative charge and (iii) results in the mutant protease having reduced tissue surface irritation relative to the modified or unmodified *Bacillus lentus* alkaline protease not having these substitutions within the 7 Å radius.

14. The method of claim 13 wherein at least one of the amino substitutions within the 7 Å radius of the substrate binding region that leads to the reduced positive charge or increased negative charge is at a position selected from 99, 154, or 211 or combinations thereof, relative to the unmodified *Bacillus lentus* alkaline protease.

15. The method of claim 14, wherein the mutant protease has one or more substitutions selected from the group consisting of R99G, R99S, R99A, L211D, L211E, S154D, and S154E.

16. The method of claim 13, wherein the mutant protease is a protease M130, or a protease M131, or both a protease M130 and a protease M131, and wherein said mutant protease is modified by one or more amino acid substitutions in its amino acid sequence at a position that lies within a 7 Å radius of the substrate binding region of the unmodified *Bacillus lentus* alkaline protease, wherein said one or more amino acid substitutions leads to a reduced positive charge or an increased negative charge.

17. The method of claim 16, wherein the mutant protease has one or more substitutions at a position selected from 99, 154, or 211 or combinations thereof relative to the unmodified *Bacillus lentus* alkaline protease.

\* \* \* \* \*

UNITED STATES PATENT AND TRADEMARK OFFICE
CERTIFICATE OF CORRECTION

PATENT NO. : 6,509,021 B1
APPLICATION NO. : 09/011889
DATED : January 21, 2003
INVENTOR(S) : Weiss et al.

It is certified that error appears in the above-identified patent and that said Letters Patent is hereby corrected as shown below:

column 9, line 24, delete "alagite", and insert therefor --alanine--.

column 9, line 28, delete "glutanic", and insert therefor --glutamic--.

column 9, line 31, after "protease", delete "as", and insert therefor --has--.

column 9, line 37, delete "L211D)", and insert therefor --L211D--.

column 9, line 45, after "more", delete "no", and insert therefor --amino--.

Signed and Sealed this

Eighth Day of August, 2006

JON W. DUDAS
*Director of the United States Patent and Trademark Office*